US012623022B1

(12) United States Patent
Hee-Hanson et al.

(10) Patent No.: US 12,623,022 B1
(45) Date of Patent: May 12, 2026

(54) MEDICAMENT DELIVERY DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB); Haiming Wu, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 19/064,323

(22) Filed: Feb. 26, 2025

(51) Int. Cl.
*A61M 5/20* (2006.01)

(52) U.S. Cl.
CPC ..... *A61M 5/2033* (2013.01); *A61M 2005/206* (2013.01); *A61M 2005/2073* (2013.01); *A61M 2005/2086* (2013.01)

(58) Field of Classification Search
CPC ............ A61M 2005/2073; A61M 5/50; A61M 5/5086; A61M 2205/276
See application file for complete search history.

(56) References Cited

U.S. PATENT DOCUMENTS

| | | | |
|---|---|---|---|
| 2,522,961 A | 9/1950 | William |
| 2,633,267 A | 3/1953 | Lebus |
| 3,886,513 A | 5/1975 | Smith et al. |
| 3,993,063 A | 11/1976 | Larrabee |
| 4,801,295 A | 1/1989 | Spencer |

| | | | |
|---|---|---|---|
| 5,045,062 A | 9/1991 | Henson |
| 5,176,275 A | 1/1993 | Bowie |
| 5,328,484 A | 7/1994 | Somers et al. |
| 5,396,051 A | 3/1995 | Kuhn et al. |
| 5,478,316 A | 12/1995 | Bitdinger et al. |
| 5,505,324 A | 4/1996 | Danico |

(Continued)

FOREIGN PATENT DOCUMENTS

| | | |
|---|---|---|
| DE | 2626811 A1 | 12/1976 |
| DE | 3921747 A1 | 1/1991 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Emily L Schmidt
(74) *Attorney, Agent, or Firm* — Fish & Richardson P.C.

(57) ABSTRACT

A medicament delivery device for injecting medicament is described. The device has a body having a proximal end and a distal end, a needle for injecting medicament, an actuation member which is movable relative to the body from a first position to a second position for dispensing medicament from the needle, a lock ring which is rotatable relative to the body from a pre-use position, in which movement of the actuation member from the first position to the second position is prevented, to a use position in which movement of the actuation member from the first position to the second position is permitted and a cap which is removably attached to the medicament delivery device. The cap has a portion which is configured to prevent rotation of the lock ring from the pre-use position to the use position when the cap is attached to the medicament delivery device.

15 Claims, 6 Drawing Sheets

(56)                References Cited

U.S. PATENT DOCUMENTS

| | | | |
|---|---|---|---|
| 5,505,706 | A | 4/1996 | Maus et al. |
| 5,536,917 | A | 7/1996 | Suppelsa et al. |
| 5,622,274 | A | 4/1997 | Bright |
| 5,738,658 | A | 4/1998 | Maus et al. |
| 5,984,899 | A | 11/1999 | D'Alessio et al. |
| 6,080,461 | A | 6/2000 | Wozniak et al. |
| 6,394,985 | B1 | 5/2002 | Lin |
| 7,762,981 | B2 | 7/2010 | Dacquay et al. |
| 7,887,506 | B1 | 2/2011 | Smolyarov et al. |
| 7,918,824 | B2 | 4/2011 | Bishop et al. |
| 8,133,198 | B2 | 3/2012 | Neer |
| 8,409,138 | B2 | 4/2013 | James et al. |
| 8,734,394 | B2 | 5/2014 | Adams et al. |
| 9,044,553 | B2 | 6/2015 | James et al. |
| 9,402,957 | B2 | 8/2016 | Adams et al. |
| 9,474,780 | B2 | 10/2016 | Bokvist et al. |
| 9,872,961 | B2 | 1/2018 | Fourt et al. |
| 10,118,001 | B2 | 11/2018 | Fourt et al. |
| 10,314,981 | B2 | 6/2019 | Sampson et al. |
| 10,350,362 | B2 | 7/2019 | Dennis, Jr. et al. |
| 10,363,377 | B2 | 7/2019 | Atterbury et al. |
| 11,298,462 | B2 | 4/2022 | Atterbury et al. |
| 11,331,432 | B2 | 5/2022 | Holmqvist et al. |
| 11,357,820 | B2 | 6/2022 | Corvari et al. |
| 11,369,751 | B2 | 6/2022 | Ruan et al. |
| 11,452,821 | B2 | 9/2022 | LaFever et al. |
| 2002/0055712 | A1 | 5/2002 | Neracher |
| 2004/0039336 | A1 | 2/2004 | Amark et al. |
| 2005/0101919 | A1 | 5/2005 | Brunnberg |
| 2005/0273061 | A1 | 12/2005 | Hommann et al. |
| 2006/0224124 | A1 | 10/2006 | Scherer |
| 2007/0270777 | A1 | 11/2007 | Dacquay et al. |
| 2008/0097311 | A1 | 4/2008 | Dacquay et al. |
| 2008/0097390 | A1 | 4/2008 | Dacquay et al. |
| 2008/0269692 | A1 | 10/2008 | James et al. |
| 2009/0036868 | A1 | 2/2009 | Pinedjian et al. |
| 2009/0281496 | A1 | 11/2009 | Matusch |
| 2010/0049125 | A1 | 2/2010 | James et al. |
| 2010/0211005 | A1 | 8/2010 | Edwards et al. |
| 2011/0034878 | A1 | 2/2011 | Radmer et al. |
| 2011/0054414 | A1 | 3/2011 | Shang et al. |
| 2011/0144594 | A1 | 6/2011 | Sund et al. |
| 2011/0202011 | A1 | 8/2011 | Wozencroft |
| 2011/0319813 | A1 | 12/2011 | Kamen et al. |
| 2011/0319864 | A1 | 12/2011 | Beller et al. |
| 2013/0237921 | A1 | 9/2013 | Lannan et al. |
| 2013/0267897 | A1 | 10/2013 | Kemp et al. |
| 2014/0236076 | A1 | 8/2014 | Marshall et al. |
| 2014/0249483 | A1 | 9/2014 | Kiilerich et al. |
| 2014/0263156 | A1 | 9/2014 | Newsom et al. |
| 2014/0276637 | A1 | 9/2014 | Massey, Jr. |
| 2015/0174325 | A1 | 6/2015 | Young et al. |
| 2015/0246180 | A1 | 9/2015 | Fenlon et al. |
| 2015/0246181 | A1* | 9/2015 | Fourt ............... A61M 5/31566 604/196 |
| 2015/0273162 | A1 | 10/2015 | Holmqvist |
| 2016/0001015 | A1 | 1/2016 | Kucuk et al. |
| 2016/0354555 | A1 | 12/2016 | Gibson et al. |
| 2016/0367763 | A1 | 12/2016 | Tschirren et al. |
| 2017/0173264 | A1 | 6/2017 | Bendek et al. |
| 2017/0215699 | A1 | 8/2017 | Ouyang et al. |
| 2017/0216526 | A1 | 8/2017 | Brereton et al. |
| 2017/0224929 | A1 | 8/2017 | Sampson et al. |
| 2017/0246403 | A1 | 8/2017 | Cowe et al. |
| 2017/0354790 | A1 | 12/2017 | Atterbury et al. |
| 2017/0361034 | A1 | 12/2017 | Scheller et al. |
| 2018/0250471 | A1* | 9/2018 | Grimoldby ......... A61M 5/3204 |
| 2018/0339114 | A1 | 11/2018 | Wendland et al. |
| 2019/0030249 | A1 | 1/2019 | Gonzalez et al. |
| 2019/0192785 | A1 | 6/2019 | Wendland et al. |
| 2019/0366000 | A1 | 12/2019 | Cowe et al. |
| 2020/0114041 | A1 | 4/2020 | Alas et al. |
| 2020/0121853 | A1 | 4/2020 | Dobson et al. |
| 2020/0139046 | A1* | 5/2020 | Jacobsen ........... A61M 5/31595 |
| 2020/0282144 | A1 | 9/2020 | Pearson |
| 2020/0316314 | A1 | 10/2020 | Buri et al. |
| 2021/0077732 | A1 | 3/2021 | Egelhofer |
| 2021/0196900 | A1 | 7/2021 | Apply et al. |
| 2022/0015429 | A1 | 1/2022 | Brown et al. |
| 2022/0176042 | A1 | 6/2022 | Belisle |
| 2022/0395640 | A1 | 12/2022 | Schwartzentruber |
| 2023/0001099 | A1 | 1/2023 | Dunn |
| 2023/0238105 | A1 | 7/2023 | Schneider et al. |
| 2023/0347074 | A1 | 11/2023 | Gavin |
| 2024/0009397 | A1 | 1/2024 | In et al. |
| 2024/0065940 | A1 | 2/2024 | Foucher et al. |

FOREIGN PATENT DOCUMENTS

| | | | |
|---|---|---|---|
| EP | 3501577 | A1 | 6/2019 |
| WO | WO 2002/047746 | A1 | 6/2002 |
| WO | WO 2004/058820 | A2 | 7/2004 |
| WO | WO 2004/068820 | A2 | 8/2004 |
| WO | WO 2005/018629 | A1 | 3/2005 |
| WO | WO 2006/003388 | A2 | 1/2006 |
| WO | WO 2006/030220 | A1 | 3/2006 |
| WO | WO 2011/109205 | A2 | 9/2011 |
| WO | WO 2015/001819 | A1 | 1/2015 |
| WO | WO 2016/081238 | A1 | 5/2016 |
| WO | WO 2018/142167 | A1 | 8/2018 |
| WO | WO 2019/074788 | A1 | 4/2019 |
| WO | WO 2020/190529 | A1 | 9/2020 |

OTHER PUBLICATIONS

Holt et al., "Domain antibodies: proteins for therapy," Trends in Biotechnology, Nov. 2003, 21(11):484-490.

Muyldermans, "Single domain camel antibodies: current status," Reviews in Molecular Biotechnology, Jun. 2001, 74(4):277-302.

Needle-based injection systems for medical use requirements and test methods, Part 1: Needle injection systems, ISO 11608 1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 1, 1989, 341(6242):544-546.

U.S. Appl. No. 19/063,738, filed Feb. 26, 2025, Alexander Hee-Hanson.

U.S. Appl. No. 19/064,399, filed Feb. 26, 2025, Alexander Hee-Hanson.

U.S. Appl. No. 19/064,354, filed Feb. 26, 2025, Alexander Hee-Hanson.

U.S. Appl. No. 19/064,379, filed Feb. 26, 2025, Alexander Hee-Hanson.

International Search Report and Written Opinion in International Appln. No. PCT/US2025/045033, mailed on Jan. 27, 2026, 10 pages.

U.S. Appl. No. 19/063,738, Alexander Hee-Hanson, filed Feb. 26, 2025.

U.S. Appl. No. 19/064,354, Alexander Hee-Hanson, filed Feb. 26, 2025.

U.S. Appl. No. 19/064,379, Alexander Hee-Hanson, filed Feb. 26, 2025.

U.S. Appl. No. 19/064,399, Alexander Hee-Hanson, filed Feb. 26, 2025.

International Search Report and Written Opinion in International Appln. No. PCT/US2025/044876, mailed on Dec. 22, 2025, 20 pages.

* cited by examiner

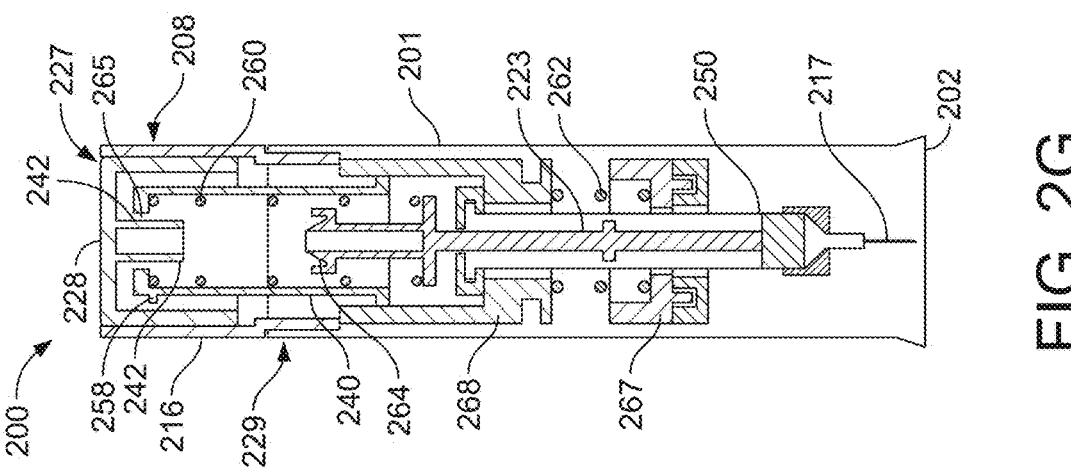
FIG. 2G
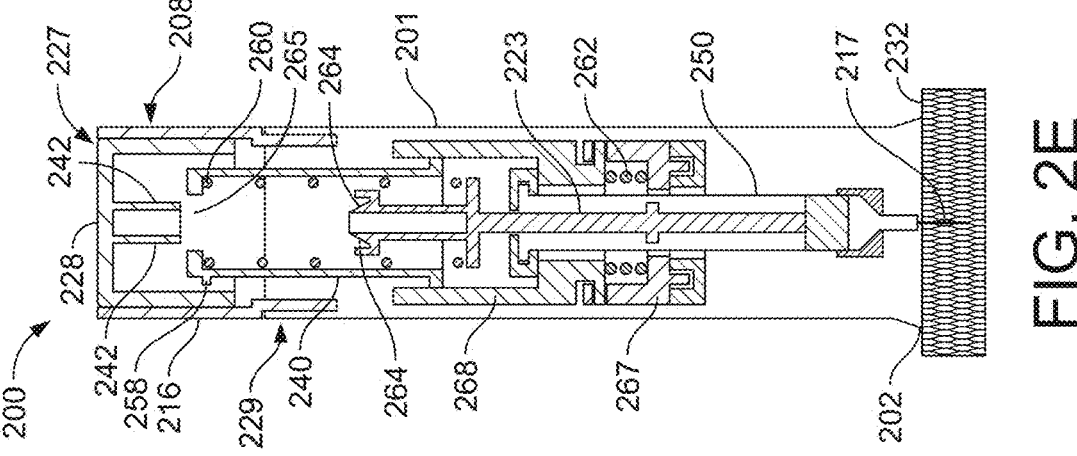
FIG. 2F
FIG. 2E

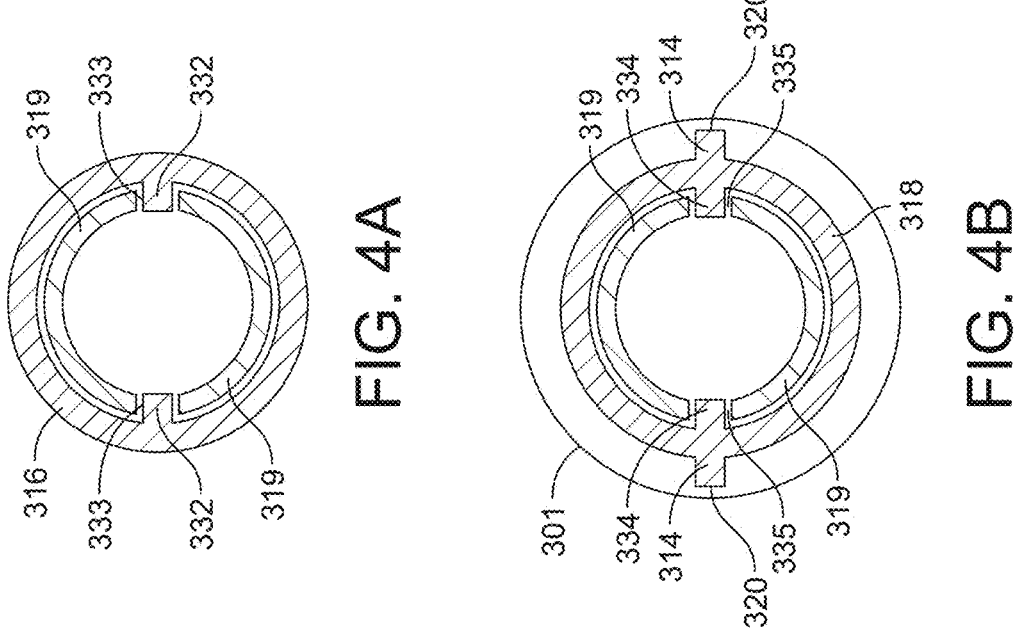
FIG. 4A
FIG. 4B
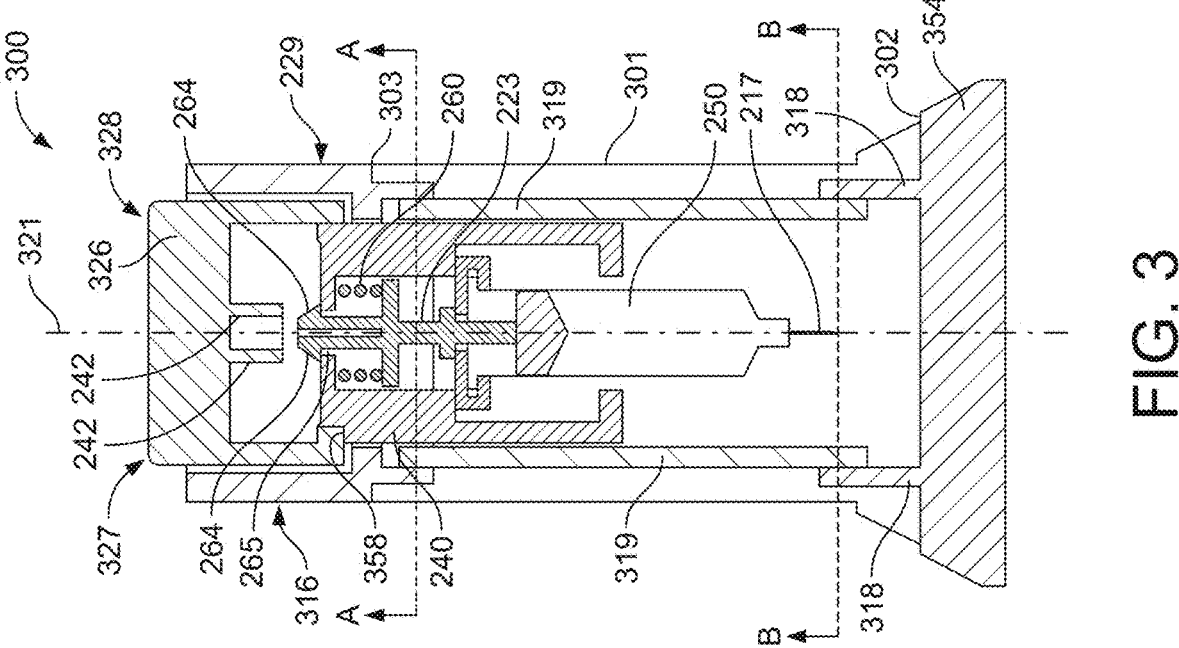
FIG. 3

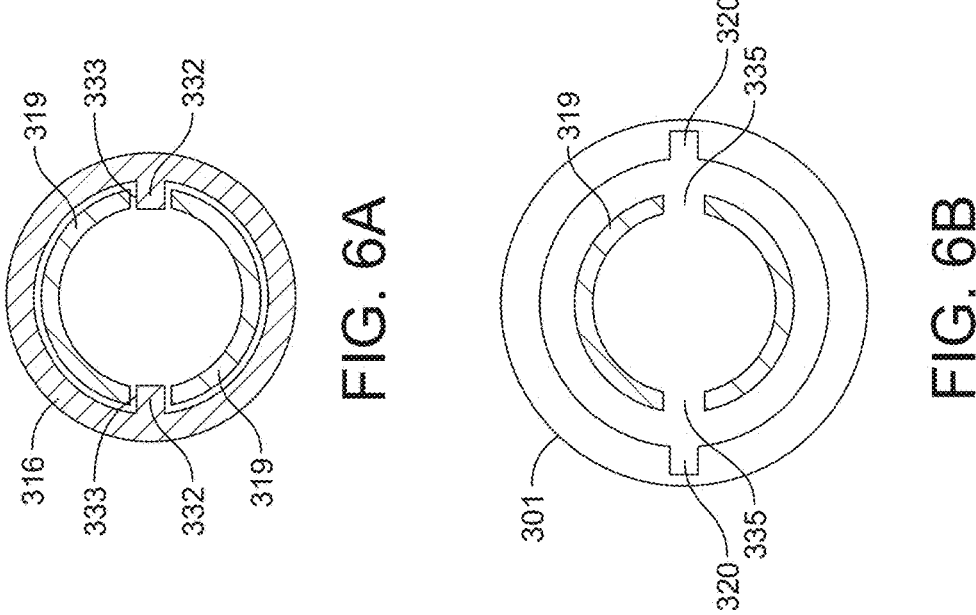
FIG. 6A
FIG. 6B
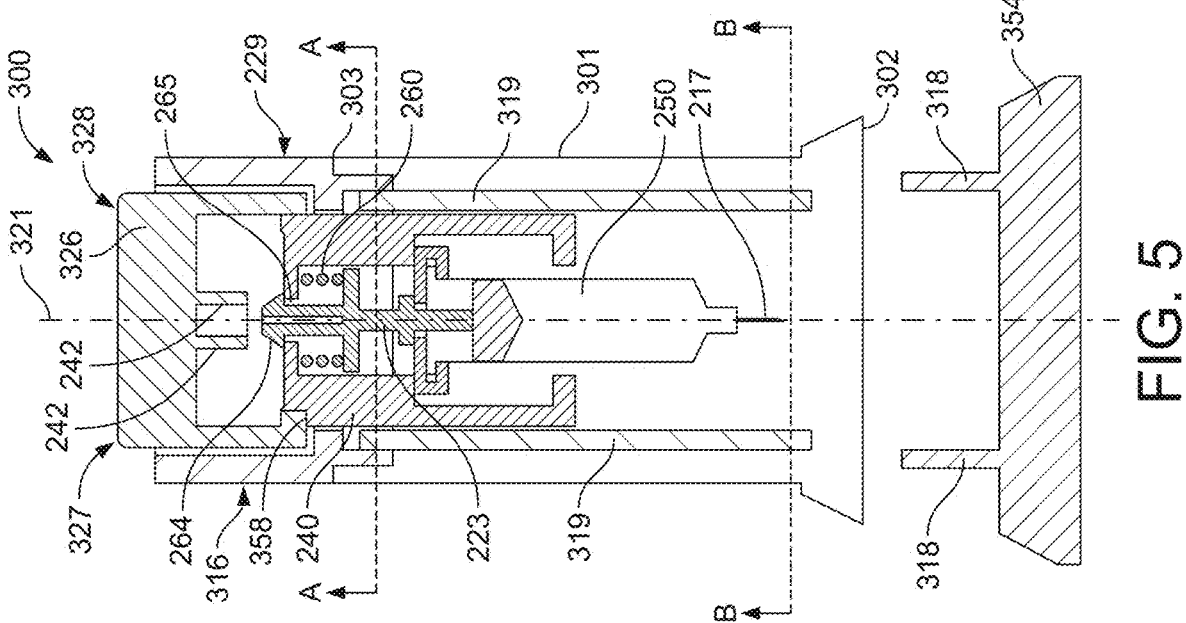
FIG. 5

MEDICAMENT DELIVERY DEVICE

TECHNICAL FIELD

The present disclosure relates to a medicament delivery device, a method of preparing a medicament delivery device for use and a method of using a medicament delivery device.

BACKGROUND

Medicament delivery devices, such as auto-injectors, are known in the art for dispensing medicament to an injection site of a patient. In some cases, the needle actuator can be depressed accidentally, for example, before the device is ready and/or in position for use. Depressing the needle actuator accidentally can cause a dose of medicament to be unintentionally dispensed. This can lead to a waste of medicament.

SUMMARY

According to a first aspect of the present disclosure, there is provided a medicament delivery device for injecting medicament, wherein the medicament delivery device comprises a body having a proximal end and a distal end; a needle for injecting medicament; an actuation member which is movable relative to the body from a first position to a second position for dispensing medicament from the needle; a lock ring which is rotatable relative to the body from a pre-use position, in which movement of the actuation member from the first position to the second position is prevented, to a use position in which movement of the actuation member from the first position to the second position is permitted; and a cap which is removably attached to the medicament delivery device, wherein the cap comprises a portion which is configured to prevent rotation of the lock ring from the pre-use position to the use position when the cap is attached to the medicament delivery device.

The cap may be removably attached to the body.

The portion may be rotationally constrained relative to the body when the cap is attached to the medicament delivery device.

One of the portion and the body may comprise a protrusion and the other of the portion and the body may comprise a recess, and wherein when the cap is attached to the medicament delivery device then the protrusion is received in the recess to constrain rotation of the portion relative to the body.

The medicament delivery device may further comprise an axially-extending component which is rotationally constrained relative to the lock ring, and wherein the portion is configured to engage the axially-extending component to prevent rotation of the lock ring to the use position when the cap is attached to the medicament delivery device.

The portion may engage the axially-extending component when the lock ring is in the pre-use position.

One of the axially-extending component and the portion may comprise a protrusion and the other of the axially-extending component and the portion may comprise a recess, and wherein the protrusion is received in the recess to constrain rotation of the axially-extending component relative to the portion.

The axially-extending component and the portion may be located radially outwards from the body.

The axially-extending component and the portion may be located radially inwards from the body.

The lock ring may comprise the axially-extending component.

The axially-extending component may be a separate component to the lock ring.

One of the axially-extending component and the lock ring may comprise a protrusion and the other of the axially-extending component and the lock ring may comprise a recess, and wherein the protrusion is received in the recess to constrain rotation of the axially-extending component relative to the lock ring.

The portion may be configured to prevent rotation the lock ring relative to the body when the cap is attached to the medicament delivery device.

The actuation member may be configured to be rotated with the lock ring when the lock ring rotates from the pre-use position to the use position.

The medicament delivery device may comprise a stop which engages the actuation member to prevent the actuation member from moving from the first position to the second position when the lock ring is in the pre-use position.

The actuation member may comprise a button which is configured to be pressed to move the actuation member from the first position to the second position.

The medicament delivery device may comprise a dispensing mechanism configured to dispense medicament from the needle, and wherein the actuation member is configured to release the dispensing mechanism when the actuation member is in the second position.

The medicament delivery device may further comprise a container containing the medicament.

According to another aspect of the present disclosure, there is provided a method of preparing a medicament delivery device for use prior to dispensing medicament from the device, the method comprising removing a cap from the medicament delivery device, wherein the cap comprises a portion configured to prevent rotation of a lock ring of the medicament delivery device from a pre-use position to a use position; and rotating the lock ring from the pre-use position to the use position.

According to another aspect of the present disclosure, there is provided a method of using a medicament delivery device, the method comprising removing a cap from the medicament delivery device, wherein the cap comprises a portion configured to prevent rotation of a lock ring of the medicament delivery device from a pre-use position to a use position; rotating the lock ring from the pre-use position to the use position; and moving an actuation member from a first position to a second position for dispensing medicament from the medicament delivery device.

When the cap is attached to the medicament delivery device then the cap may cover the distal end of the body for preventing access to the needle.

The needle may be for protruding from the distal end of the body for injecting medicament. The needle may be for protruding from the distal end of the medicament delivery device for injecting medicament. The needle may be configured to protrude from the distal end of the body. The needle may have a distal free end for injecting medicament.

The portion may be a proximally-extending portion.

The portion may be rotationally fixed relative to the body when the cap is attached to the medicament delivery device The portion may be configured to prevent rotation of the lock ring relative to the body when the cap is attached to the medicament delivery device.

When the cap is attached to the body then the protrusion may be received in the recess to prevent rotation of the portion relative to the body.

The axially-extending component may be rotationally fixed relative to the lock ring.

The protrusion may be received in the recess to prevent rotation of the axially-extending component relative to the portion.

The portion may be a proximally-extending portion.

The protrusion may be received in the recess to prevent rotation of the axially-extending component relative to the lock ring.

The button may be provided at the proximal end of the medicament delivery device.

The actuation member may be distally movable relative to the body from the first position to the second position.

The portion may comprise a sleeve.

The actuation member may be configured to release the dispensing mechanism when the actuation member is in the second position. The actuation member may be configured to engage the dispensing mechanism to release the dispensing mechanism when the actuation member is in the second position.

The dispensing mechanism may be further configured to cause the needle to move distally from a needle pre-use position to a needle injection position in which the needle protrudes from the distal end of the body when the dispensing mechanism is released.

Moving the actuation member from the first position to the second position may comprise pressing the actuation member.

According to another aspect of the present disclosure, there is provided a method of manufacturing or assembling a medicament delivery device, wherein the medicament delivery device is defined in claim 1. Further optional features of the medicament delivery device are described and/or contemplated here.

According to another aspect of the present disclosure, there is provided a method of manufacturing or assembling a medicament delivery device, wherein the medicament delivery device has the features of any of the medicament delivery devices described and/or contemplated herein.

BRIEF DESCRIPTION OF THE DRAWINGS

Embodiments will now be described, by way of example only, with reference to the accompanying drawings, in which:

FIG. 2E is a schematic view of the device of FIG. 2A with the button having been pressed to release the dispensing mechanism;

FIG. 2F is a schematic view of the device of FIG. 2A showing the needle having retracted within the device after a dose has been delivered;

FIG. 2G is a schematic view of the device of FIG. 2A showing the device removed from the injection site after the needle has retracted within the device after delivery of the medicament;

FIG. 3 is a schematic view of parts of a medicament delivery device with the cap attached to the body according to an embodiment of the disclosure;

FIG. 4A is cross-sectional view of the device of FIG. 3 taken along the line A-A from FIG. 3;

FIG. 4B is cross-sectional view of the device of FIG. 3 taken along the line B-B from FIG. 3;

FIG. 5 is a schematic view of the device of FIG. 3 with the cap removed from the body;

FIG. 6A is cross-sectional view taken along the line A-A from FIG. 5;

FIG. 6B is cross-sectional view taken along the line B-B from FIG. 5;

DETAILED DESCRIPTION

Figures 1A, 1B:
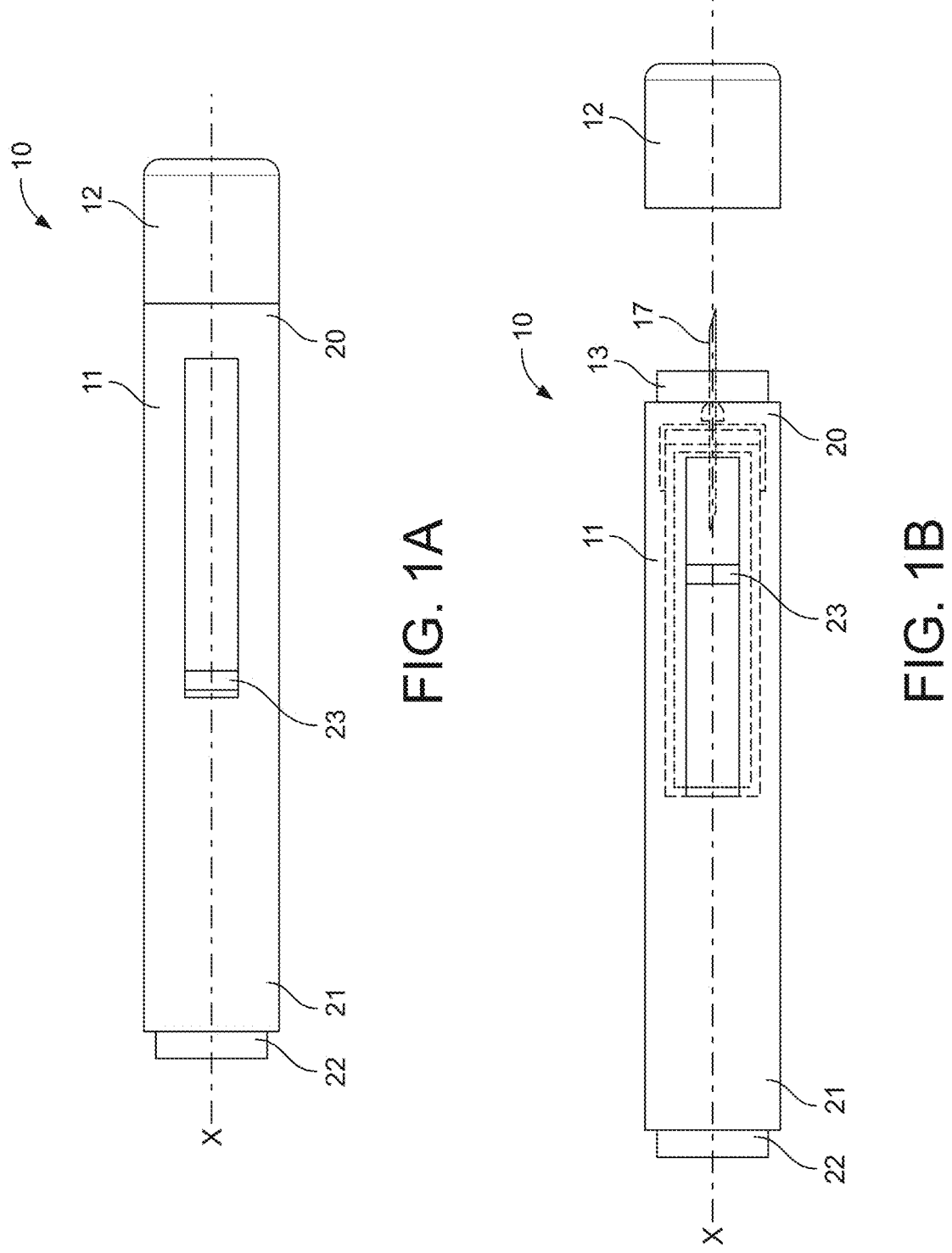
FIG. 1A is a schematic view of a medicament delivery device with a cap attached.
FIG. 1B is a schematic view of the medicament delivery device of FIG. 1A with the cap removed.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy.

One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the auto- mated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, acti- vation of a first automated function may activate at least two of needle insertion, medicament injection, and needle retrac- tion. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medica- ment (as typically found in an auto-injector) and a dose setting mechanism (as typically found in a pen-injector).

According to some embodiments of the present disclo- sure, an exemplary drug delivery device 10 is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. A user typically removes the cap 12 from the housing 11 before the device is operated.

10 As shown, the housing 11 is substantially cylindrical and has a substantially constant diameter along the longi- tudinal axis X. The housing 11 has a distal region 20 and a proximal region 21. The term "distal" refers to a location that is relatively closer to a site of injection, and the term "proximal" refers to a location that is relatively further away from the injection site.

The device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from the distal region 20 of the housing 11.

Insertion of the needle 17 can occur via several mecha- nisms. For example, the needle 17 may be fixedly located relative to the housing 11 and initially be located within an extended needle sleeve 13. Proximal movement of the sleeve 13 by placing a distal end of the sleeve 13 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of sleeve 13 or by another form of activation, for example, a button 22. As shown in FIGS. 1A & 1B, the button 22 is located at a proximal end of the housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medi- cament from the syringe through the needle 17. In some embodiments, a drive spring (not shown) is under compres- sion before the device 10 is activated. A proximal end of the drive spring can be fixed within the proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on piston 23 to move it in a distal direction. Such distal movement acts to compress the liquid medicament within the syringe, forcing it out of the needle 17.

Following injection, the needle 17 can be retracted within the sleeve 13 or the housing 11. Retraction can occur when the sleeve 13 moves distally as a user removes the device 10 from a patient's body. This can occur as the needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

FIGS. 2A to 2G show the sequential steps of operating a medicament delivery device 200. The medicament delivery device 200 is an autoinjector.

The device 200 comprises a body 201, a syringe 250 having a needle 217 and an axially moveable plunger 223 for dispensing medicament from the syringe 250. The device comprises a cap 254 which is removably attached to the body 201 and covers a distal end 202 of the body 201 for preventing access to the needle 217. The device has a needle shield 266 that covers the needle 217 before use. The needle shield 266 is attached to the cap 254.

The medicament delivery device 200 has a dispensing mechanism 229. The medicament delivery device 200 has an actuation member 227 which is configured to release the dispensing mechanism 229. The actuation member 227 is configured to engage the dispensing mechanism 229 to release the dispensing mechanism 229

The dispensing mechanism 229 is configured to cause the needle 217 to move distally from a needle pre-use position, in which the needle 217 is recessed within the body 201, to an injection position in which the needle 217 protrudes from the distal end 202 of the body 201 when the dispensing mechanism 229 is released.

The dispensing mechanism 229 is configured to dispense the medicament from the needle 217 when the needle 217 is in the injection position.

Figures 2A, 2B, 2C, 2D:
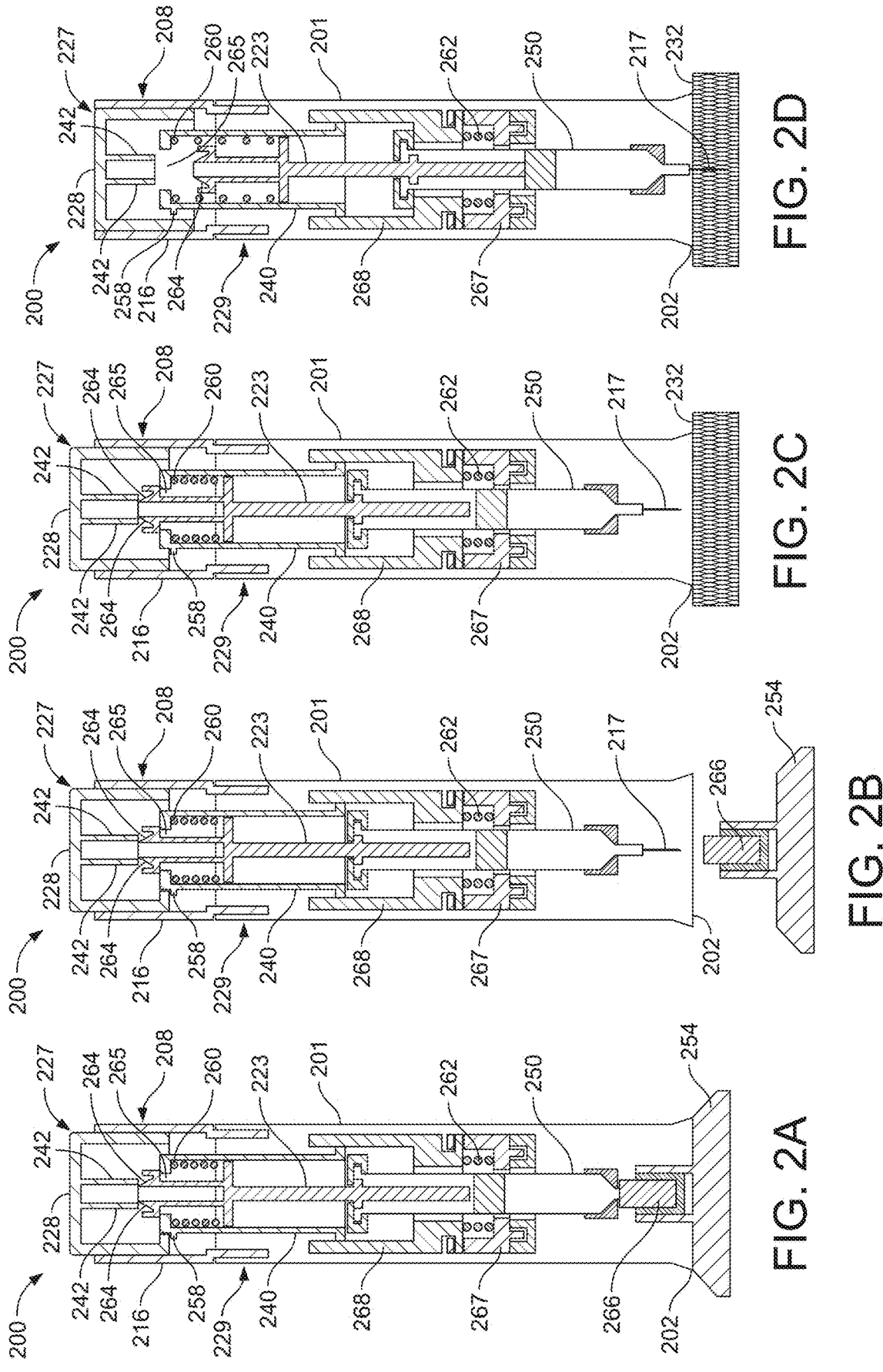
FIG. 2A is a schematic view of a medicament delivery device prior to use (i.e. in a pre-use configuration)
FIG. 2B is a schematic view of the device of FIG. 2A with the cap removed.
FIG. 2C is a schematic view of the device of FIG. 2A showing the device placed at an injection site.
FIG. 2D is a schematic view of the device of FIG. 2A with the button having been pressed to release the dispensing mechanism.

As shown in FIGS. 2B-2C, in order to deliver a dose of medicament to an injection site, the cap 254 is removed (FIG. 2B) and the device is placed at an injection site 232 (FIG. 2C).

The actuation member 227 comprises a button 228 and is prevented from being depressed by a stop 258. The stop is provided on the spring guide 240, for example.

The device has a locking member 208 in the form of a lock ring 216 which is rotatable by a user about a longitudinal axis of the device. The actuation member 227 is keyed to the lock ring 216 so that the actuation member 227 rotates with the lock ring 216. The lock ring 216 is rotatable from a pre-use position, in which distal movement of the button 228 is prevented, to a use position in which distal movement of the button 228 is permitted.

When the lock ring 216 is in the pre-use position then the stop 258 engages the button 228 to prevent the button 228 from being depressed.

In order to allow the button 228 to be depressed, the lock ring 216 is rotated about the longitudinal axis of the device from the pre-use position to the use position. The rotation of the lock ring 216 also rotates the actuation member 227 to a position in which the stop 258 no longer prevents the button 228 from being depressed as shown, for example, in FIG. 2C.

Turning now to FIG. 2D, the user then presses the button 228 to release the dispensing mechanism 229 for dispensing medicament from the device. The dispensing mechanism 229 has a plunger 223 and a bias in the form of a compression spring 260. The plunger 223 is biased distally by the spring 260.

The dispensing mechanism 229 is at least partially housed within the spring guide 240. The plunger 223 has a release member which has proximally-extending clips 264. The spring 260 is retained in the compressed position by virtue of the clips 264 which protrude through a proximal opening 265 in the spring guide 240. The clips 264 engage the spring guide 240 for maintaining the plunger 223 in a proximal position.

The actuation member 227 has a firing member comprising a pair of protrusions 242 which engage with the clips 264 when the button 228 is depressed to flex the clips 264 radially inwardly thereby allowing the clips 264 to move distally through the proximal opening 265 to release the spring 260.

When the dispensing mechanism 229 is released, then the syringe 250 is released for distal axial movement towards the injection site 232 such that the needle 217 moves from the needle pre-use retracted position to an exposed (or "uncovered" or "injection") position for delivering medicament to the injection site 232 under the biasing force of the compression spring 260.

Depressing the button 228 releases the plunger 223 which, biased by the bias 260, moves along the syringe 250 towards the distal end of the device 200 to force medicament within the syringe 250 through the needle 217, thereby delivering a dose of medicament as shown, for example in FIG. 2E.

As shown in FIG. 2F, once the dose of medicament has been delivered, a medicament container bias 262, embodied by a further spring 262, then causes the needle 217 to move axially back to the retracted position, away from the injection site 232 in a proximal direction. The plunger 223 flexes a clip (not shown) on a first collar 267 which allows the first collar 267 to rotate relative to the body 201 and relative to a second collar 268. The first collar 267 rotates from a first position in which the second collar 268 is axially coupled to the first collar 267, into a second position in which the second collar 268 is free to move axially relative to the first collar 267. For example, the second collar 268 may comprise a radially protruding coupling element configured to be received in or engage with a corresponding receiving portion of the first collar 267, such that rotating the first collar 267 from the first position into the second position causes the coupling element to be moved out from the receiving portion, to allow the second collar 268 to move axially relative to the first collar 267. Axial movement of the second collar 268 permits the needle 217 to be retracted.

As shown in FIG. 2G, the device 200 is then removed from the injection site 232, for disposal.

FIG. 3 is a schematic view of parts of a medicament delivery device 300 in accordance with an embodiment of the disclosure. The medicament delivery device 300 has corresponding features as described and/or contemplated herein in relation to the medicament delivery device 200. The same reference numerals are used to annotate corresponding features of the medicament delivery device 300 as for the medicament delivery device 200.

The medicament delivery device 300 has a body 301 having a proximal end 303 and a distal end 302, a needle 217 for injecting medicament, and an actuation member 327 which is movable relative to the body 301 from a first position to a second position for dispensing medicament from the needle 217. FIG. 3 shows the actuation member 327 in an example first position. The actuation member 327 is distally movable relative to the body 301 from the first position to the second position.

The needle 217 is for protruding from the distal end of the medicament delivery device for injecting medicament. The needle 217 is for protruding from the distal end 302 of the body for injecting medicament. The needle 217 is configured to protrude from the distal end of the body 301 when the actuation member is in the second position. The needle 217 has a distal free end for injecting medicament.

The needle 217 is part of a syringe 250 which contains the medicament. The syringe 250 can be seen as a container containing the medicament. The syringe 250 can be said to comprise the needle 217. Another embodiment may comprise a container which contains medicament, wherein the container is initially separated from the needle before the actuation member is moved from the first position to the second position. The container may be a cartridge of medicament. Movement of the actuation member from the first position to the second position may cause the proximal end of the needle to pierce the container.

The medicament delivery device 300 has a lock ring 316 which is rotatable relative to the body 301 from a pre-use position, in which movement of the actuation member 327 from the first position to the second position is prevented, to a use position in which movement of the actuation member 327 from the first position to the second position is permitted. The lock ring 316 is rotatable about the longitudinal axis 321 of the device.

The medicament delivery device 300 may have corresponding features as described and/or contemplated in relation to FIGS. 2A to 2G. For example, the lock ring 316, actuation member 327 and spring guide 240 may have corresponding features to those described and/or contemplated in relation to the lock ring 216, actuation member 227 and spring guide 240 of FIGS. 2A to 2G.

The actuation member 327 is configured to be rotated with the lock ring 316 when the lock ring 316 rotates from the pre-use position to the use position. For example, the actuation member 327 is keyed to the lock ring 316.

The medicament delivery device 300 has a stop 358 which engages the actuation member 327 to prevent the actuation member 327 from moving from the first position to the second position when the lock ring 316 is in the pre-use position. The stop 358 may be provided on an inner housing 240 which is also referred to herein as a spring guide.

The rotation of the lock ring 316 from the pre-use position to the use position rotates the actuation member 327 to a position in which the stop no longer prevents the actuation member 327 from being moved from the first position to the second position.

In another embodiment, different features are provided to prevent the actuation member 327 from moving from the first position to the second position when the lock ring is in the pre-use position. For example, the stop may be provided on another component of the medicament delivery device.

The medicament delivery device 300 has a cap 354 which is removably attached to the body 301. When the cap 354 is attached to the body 301 then the cap 354 covers the distal end 302 of the body 301 for preventing access to the needle 217. The cap 354 may include one or more apertures therein.

The cap 354 has a portion 318 which is configured to prevent rotation of the lock ring 316 from the pre-use position to the use position when the cap 354 is attached to the body 301. The portion 318 is a sleeve, for example a circular sleeve. In another embodiment the portion 318 may be a proximally-extending arm. The portion 318 may be described as a proximally-extending portion. The proximally-extending portion may extend into the body 301 when the cap 354 is attached to the body 301.

The portion 318 is configured to prevent rotation of the lock ring 316 relative to the body 301 when the cap 354 is attached to the body 301. In another embodiment the portion 318 may allow a limited amount of rotation of the lock ring 316 relative to the body 301 provided that the portion 318 prevents the lock ring 316 from reaching the use position.

In another embodiment the cap 354 is attached to another component of the medicament delivery device 300.

FIG. 4B shows a cross-section taken along the line B-B of FIG. 3. As can be seen in FIG. 4B, the portion 318 has a protrusion 314 and the body 301 has a recess 320. When the cap 354 is attached to the body 301 then the protrusion 314 is received in the recess 320 to constrain rotation of the portion 314 relative to the body 301. The protrusion 314 is a radially-extending protrusion. The protrusion 314 may be referred to as a first protrusion and the recess 320 may be referred to as a first recess.

The protrusion 314 and the recess 320 have the same or a substantially similar width. The protrusion 314 is received in the recess 320 to prevent rotation of the portion 318 relative to the body 301. The portion 318 is rotationally fixed relative to the body 301.

In another embodiment the recess 320 may be wider than the protrusion 314. The portion 318 and the body 301 are still rotationally constrained but there may be a small degree of movement between the portion 318 and the body 301.

The recess 320 may be an aperture in the body 301 or the proximally-extending portion 318. In another embodiment, the recess 320 may be a portion of reduced thickness of the body 301 or the proximally-extending portion 318.

In another embodiment the proximally-extending portion 318 is rotationally constrained relative to the body by a friction fit.

The protrusion 314 and recess 320 can be seen to constitute a pair. The medicament delivery device 300 has two pairs of protrusions 314 and recesses 320 but in another embodiment just a single protrusion 314 and recess 320 may be provided or more than two pairs of protrusions 314 and recesses 320 may be provided.

In another embodiment (not shown), the body 301 has the protrusion 314 and the portion 318 has the recess 320. When the cap 354 is attached to the body 301 then the protrusion 314 is received in the recess 320 to rotationally constrain movement of the portion 314 relative to the body 301.

In another embodiment the protrusion 314 may be an axially-extending protrusion which is received in an axially-extending recess for rotationally constraining the portion 318 relative to the body 301.

The medicament delivery device 300 has an axially-extending component 319 which is rotationally constrained relative to the lock ring 316. The axially-extending component 319 is rotationally fixed relative to the lock ring 316 but in another embodiment there may be a small degree of rotational movement between the axially-extending component 319 and the lock ring 316. The axially-extending component 319 is a sleeve, for example a cylindrical sleeve. In another embodiment, the axially-extending component may be an axially-extending arm.

FIG. 4A shows a cross-section taken along the line A-A of FIG. 3. As can be seen in FIG. 4A, the lock ring 316 has a protrusion 332 and the axially-extending component 319 has a recess 333. The protrusion 332 is received in the recess 333 to rotationally constrain the axially-extending component 319 relative to the lock ring 316. The protrusion 332 is received in the recess 333 to prevent rotation of the lock ring 316 relative to the axially-extending component 319. The protrusion 332 and the recess 333 have the same or a substantially similar width. In another embodiment there may be a small degree of rotation between the lock ring 316 and the axially-extending component 319. For example the recess 333 may be wider than the protrusion 332.

The protrusion 332 is a radially-extending protrusion. In another embodiment (not shown) the protrusion 332 may be an axially-extending protrusion which is received in an axially-extending recess for rotationally constraining the axially-extending component 319 relative to the lock ring 316. The protrusion 332 may be referred to as a second protrusion and the recess 333 may be referred to as a second recess.

The recess 333 may be an aperture in the axially-extending component 319 or the lock ring 316. In another embodiment, the recess 333 may be a portion of reduced thickness of the axially-extending component 319 or the lock ring 316.

In another embodiment the axially-extending component 319 is rotationally constrained relative to the lock ring 316 by a friction fit.

The protrusion 332 and recess 333 can be seen to constitute a pair. The medicament delivery device 300 has two pairs of protrusions 332 and recesses 333 but in another embodiment just a single protrusion 332 and recess 333 may be provided or more than two pairs of protrusions 332 and recesses 333 may be provided.

In another embodiment (not shown), the axially-extending component 319 has the protrusion 332 and the lock ring 316 has the recess 333.

The axially-extending component 319 is a separate component to the lock ring 316. In another embodiment (not shown), the lock ring 316 comprises the axially-extending component 319 for example the axially-extending component 319 may be integrally formed with the lock ring 316.

The lock ring 316 comprises a sleeve, for example a circular sleeve.

The portion 318 engages the axially-extending component 319 when the lock ring 316 is in the pre-use position. In another embodiment, the portion 318 may engage the axially-extending component 319 when the lock ring 316 has moved away from the pre-use position but before the lock 316 reaches the use position.

As can be seen in FIG. 4B, the portion 318 has a protrusion 334 and the axially-extending component 319 has a recess 335. The protrusion 334 is received in the recess 335 to constrain rotation of the portion 318 relative to the axially-extending component 319. The protrusion 334 is received in the recess 335 to prevent rotation of the portion 318 relative to the axially-extending component 319. The portion 318 is rotationally fixed relative to the axially-extending component. The protrusion 334 and recess 335 have the same or a substantially similar width.

In another embodiment there may be a small degree of rotational movement between the portion 318 and the axially-extending component 319. The recess 335 may be wider than the protrusion 334. The protrusion 334 may be referred to as a third protrusion and the recess 335 may be referred to as a third recess.

The protrusion 334 is a radially-extending protrusion. In another embodiment (not shown) the protrusion 334 may be an axially-extending protrusion which is received in an axially-extending recess for rotationally constraining or rotationally fixing the portion 318 relative to the axially-extending component 319.

The protrusion 334 and recess 335 can be seen to constitute a pair. The medicament delivery device 300 has two pairs of protrusions 334 and recesses 335 but in another embodiment just a single protrusion 334 and recess 335 may be provided or more than two pairs of protrusions 334 and recesses 335 may be provided.

The recess 335 may be an aperture in the axially-extending component 319 or the proximally-extending portion 318. In another embodiment, the recess 335 may be a portion of reduced thickness of the axially-extending component 319 or the proximally-extending portion 318.

In another embodiment the axially-extending component 319 is rotationally constrained relative to the proximally-extending portion 318 by a friction fit.

In another embodiment (not shown), the axially-extending component 319 has the protrusion 334 and the proximally-extending component 318 has the recess 335.

In the medicament delivery device 300, the axially-extending component 319 and the portion 318 are located radially inwards from the body 301. However, in another embodiment, the axially-extending component 319 and the portion 318 are located radially outwards from the body 301.

The actuation member 327 has a button 326 which is configured to be pressed to move the actuation member 327 from the first position to the second position.

The button 326 is provided at the proximal end 328 of the medicament delivery device. In another embodiment (not shown) the button is provided on a lateral side of the medicament delivery device.

The medicament delivery device 300 has a dispensing mechanism 229 which is configured to dispense medicament from the needle 217. The actuation member 327 is configured to release the dispensing mechanism 229, for example by engaging the dispensing mechanism 229, when the actuation member 327 is in the second position. The dispensing mechanism 229 is further configured to cause the needle 217 to move distally from a needle pre-use position to a needle injection position in which the needle 217 protrudes from the distal end 302 of the body 301 when the dispensing mechanism 229 is released.

The medicament delivery devices described herein, including the medicament delivery device 300, may have some or all of the features as described in relation to the medicament delivery device 200.

The dispensing mechanism 229 may have the some or all of the features as described and/or contemplated in relation to FIGS. 2A to 2G.

In another embodiment, the dispensing mechanism may have alternative or additional features to those described and/or contemplated in relation to FIGS. 2A to 2G. The dispensing mechanism may have features as described and/or contemplated herein, for example in relation to FIGS. 1A and 1B.

The dispensing mechanism provides one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

The medicament delivery device can include various types of safety syringe, pen-injector, or auto-injector. The device can include a cartridge-based system that requires piercing a sealed ampule before use.

Distal movement of the actuation member may cause automatic dispensing of the medicament from the device and/or distal movement of the actuation member may cause the distal movement of the needle from a needle pre-use position to a needle injection position. The dispensing mechanism may be configured to dispense medicament from the needle when the dispensing mechanism is released.

In the needle pre-use position the needle may be flush with the distal end of the body or the needle may be recessed within the body. In another embodiment the needle may be fixed in position relative to the body.

In another device, different features may be provided to prevent the actuation member from moving distally. For example, the stop may be provided on another component of the medicament delivery device.

FIG. 5 is a schematic view of the medicament delivery device 300 of FIG. 3 with the cap 354 removed from the body 301. FIG. 6A is cross-sectional view taken along the line A-A from FIG. 5 and FIG. 6B is cross-sectional view of the device taken along the line B-B from FIG. 5.

The portion 318 no longer prevents rotation of the lock ring 316 from the pre-use position to the use position. As can be seen in FIG. 6b, for example, the axially-extending component 319 is free to rotate relative to the body 301. Since the axially-extending component 319 is rotationally constrained or fixed relative to the lock ring 316 then the lock ring 316 is also free to rotate relative to the body 301 to the use position.

In use, the cap 354 is removed from the body 301, for example by a user. The lock ring 316 is then rotated from the pre-use position to the use position. The button 326 is then pressed, for example by the user, when the medicament delivery device 300 is held against an injection site to dispense the medicament via the needle 217.

The portion 318 prevents the user from accidentally dispensing the medicament from the needle 217 before the cap 354 has been removed from the device since the lock ring 316 is prevented from rotating to the use position until the cap 354 has been removed from the medicament delivery device. The actuation member 327 is prevented from being moved from the first position to the second position until the lock ring 316 has been rotated to the use position. The actuation member releases the dispensing mechanism, for example by engaging the dispensing mechanism, when the actuation member is in the second position.

A method of using the medicament delivery device 300 comprises removing the cap 354 from the medicament delivery device. The medicament delivery device may have any of the features described and/or contemplated herein. The method then comprises rotating the lock ring 316 from the pre-use position to the use position. The method may further comprise moving the actuation member from the first position to the second position. Moving the actuation member from the first position to the second position may comprise a user pressing the button 326.

Figure 7B:
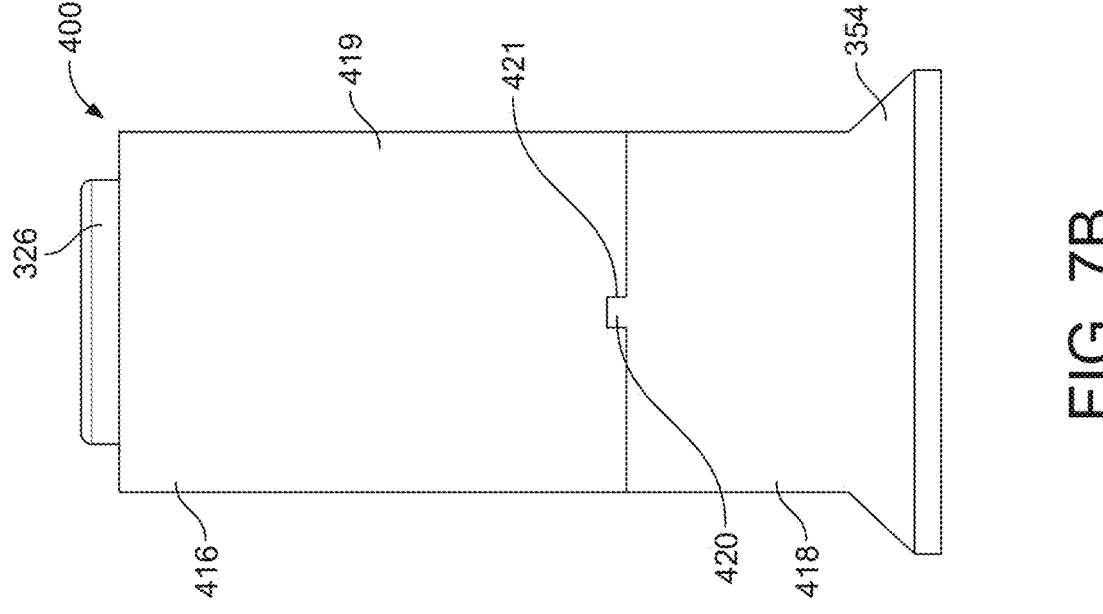
FIG. 7B is a side view of the device of FIG. 7A.
Figure 7A:
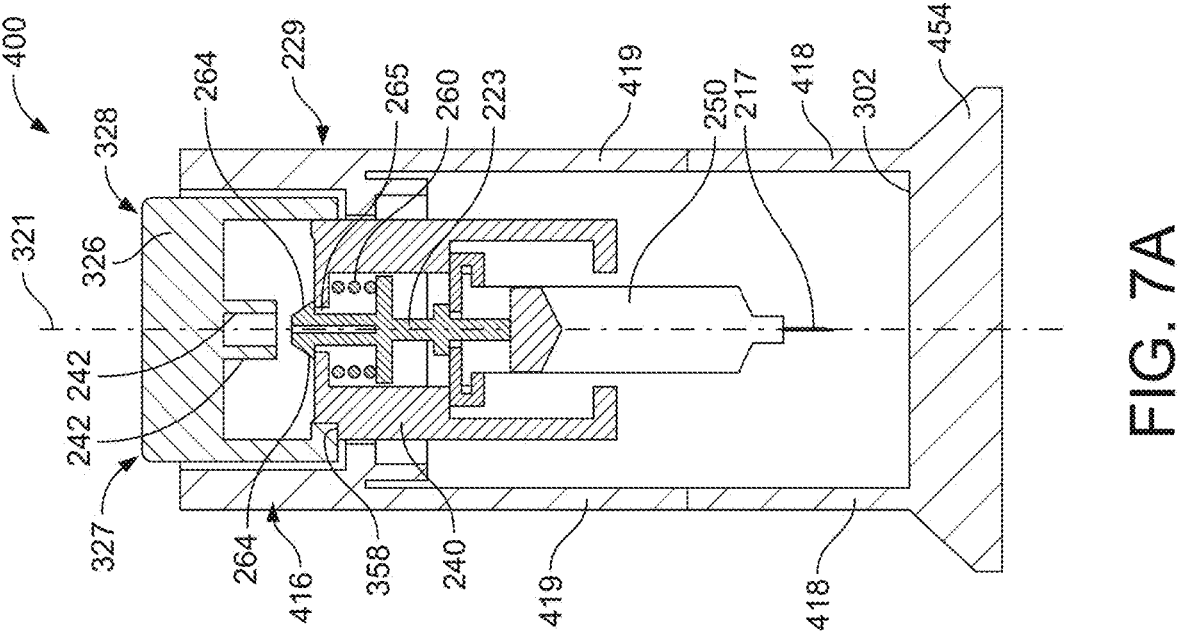
FIG. 7A is a schematic view of parts of a medicament delivery device according to another embodiment of the disclosure.

FIG. 7A is a schematic view of parts of a medicament delivery device 400 in accordance with an embodiment of the disclosure. FIG. 7B is a side view of the medicament delivery device 400 of FIG. 7A. The medicament delivery device 400 has corresponding features as described and/or contemplated herein in relation to the medicament delivery device 300 and/or the medicament delivery device 200. The same reference numbers are used to annotate corresponding features of the medicament delivery device 400 as for the medicament delivery device 300 and the medicament delivery device 200.

The medicament delivery device 400 has a lock ring 416 which is rotatable relative to the body 301 from a pre-use position, in which movement of the actuation member 327 from the first position to the second position is prevented, to a use position in which movement of the actuation member 327 from the first position to the second position is permitted. The lock ring 416 is rotatable about the longitudinal axis 321 of the device. The lock ring 416, actuation member 327 and spring guide 240 have corresponding features to those described and/or contemplated herein, for example in relation to the medicament delivery device 300 and/or in relation to the lock ring 216, actuation member 227 and spring guide 240 of FIGS. 2A to 2G.

The actuation member 327 is configured to be rotated with the lock ring 416 when the lock ring 416 rotates from the pre-use position to the use position. For example, the actuation member 327 is keyed to the lock ring 416.

The medicament delivery device 400 has a stop 358 which engages the actuation member 327 to prevent the actuation member 327 from moving from the first position to the second position when the lock ring 416 is in the pre-use position. The stop 358 may be provided on the spring guide 240.

The rotation of the lock ring 416 from the pre-use position to the use position rotates the actuation member 327 to a position in which the stop no longer prevents the actuation member 327 from being moved from the first position to the second position.

In another embodiment, different features are provided to prevent the actuation member 327 from moving from the first position to the second position when the lock ring is in the pre-use position. For example, the stop may be provided on another component of the medicament delivery device.

The medicament delivery device 400 has a cap 454 which is removably attached to the body 301. When the cap 454 is attached to the body 301 then the cap 454 covers the distal end 302 of the body 301 for preventing access to the needle 217.

In another embodiment the cap 454 is attached to another component of the medicament delivery device.

The cap 454 has a portion 418 which is configured to prevent rotation of the lock ring from the pre-use position to the use position when the cap 454 is attached to the body 301.

The portion 418 is a sleeve, for example a circular sleeve. In another embodiment the portion 418 may be a proximally-extending arm. The portion 418 may be described as a proximally-extending portion. The proximally-extending portion may extend outside of the body 301 when the cap 454 is attached to the body 301.

The portion 418 is configured to prevent rotation of the lock ring 416 relative to the body 301 when the cap 454 is attached to the body 301. In another embodiment the portion 418 may allow a limited amount of rotation of the lock ring 416 relative to the body 301 provided that the portion 418 prevents the lock ring 416 from reaching the use position.

The portion 418 is rotationally constrained or rotationally fixed relative to the body 301 when the cap 454 is attached to the body 301. For example, one of the portion 418 and the body 301 may have a protrusion and the other of the portion 418 and the body may have a recess, wherein the protrusion is received in the recess when the cap 454 is attached to the body 301 to constrain or prevent rotation of the portion 418 relative to the body 301.

The lock ring 416 comprises the axially-extending component 419 for example the axially-extending component 419 may be integrally formed with the lock ring 416. In another embodiment, the axially-extending component 419 may be a separate component to the lock ring 416. The axially-extending component 419 and the lock ring 416 may be rotationally constrained or rotationally fixed relative to each other as described and/or contemplated above in relation to the medicament delivery device 300.

The portion 418 engages the axially-extending component 419 when the lock ring is in the pre-use position. In another embodiment, the portion 418 may engage the axially-extending component 419 when the lock ring 416 has moved away from the pre-use position but before the lock 416 reaches the use position.

As can be seen in FIG. 7B, the portion 418 has a protrusion 420 and the axially-extending component 419 has a recess 421. The protrusion 420 is received in the recess 421 to constrain rotation of the portion 418 relative to the axially-extending component 419. The protrusion 420 is received in the recess 421 to prevent rotation of the portion 418 relative to the axially-extending component 419. The portion 418 is rotationally fixed relative to the axially-extending component. The width of the recess 421 is the same or substantially similar to the width of the protrusion 420.

In another embodiment there may be a small degree of rotational movement permitted between the portion 418 and the axially-extending component 419. For example the recess 421 may be wider than the protrusion 420.

The protrusion 420 is an axially-extending protrusion. The recess 421 is an axially-extending recess.

The protrusion 420 and recess 421 form a pair. A single pair may be present in the device or multiple pairs of protrusions 420 and recesses 421 may be provided for example each of the pairs may be spaced around the circumference of the device.

In another embodiment (not shown), the axially-extending component 419 has the protrusion 420 and the proximally-extending component 418 has the recess 421.

The recess 421 may be an aperture in the axially-extending component 419 or the proximally-extending portion 418. In another embodiment, the recess 421 may be a portion of reduced thickness of the axially-extending component 419 or the proximally-extending portion 418.

In another embodiment the axially-extending component 419 is rotationally constrained relative to the proximally-extending portion 418 by a friction fit.

In the medicament delivery device 400, the axially-extending component 419 and the portion 418 are located radially outwards from the body 301. However, in another embodiment, the axially-extending component 419 and the portion 418 are located radially inwards from the body 301.

The medicament delivery device 400 has a dispensing mechanism 229 which is configured to dispense medicament from the needle 217. The actuation member 327 is configured to release the dispensing mechanism 229, for example by engaging the dispensing mechanism 229, when the actuation member 327 is in the second position.

The dispensing mechanism 229 is further configured to cause the needle to move distally from a needle pre-use position to a needle injection position in which the needle 217 protrudes from the distal end of the body when the dispensing mechanism is released.

As noted above, the dispensing mechanism 229 may have alternative or additional features to those described and/or contemplated in relation to FIGS. 2A to 2G. The dispensing mechanism may have features as described and/or contemplated herein, for example in relation to FIGS. 1A and 1B.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin and Des (B30) human insulin.

Examples of insulin derivatives are, for example, B29-N-myristoyl-des (B30) human insulin, Lys (B29) (N-tetra-decanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspo-glutide, Albiglutide (Syncria®), Dulaglutide (Trulicity®), rExendin-4, CJC-1134-PC, PB-1023, TTP-054, Lan-glenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercho-lesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutro-pin, Choriongonadotropin, Menotropin), Somatropine (So-matropin), Desmopressin, Terlipressin, Gonadorelin, Trip-torelin, Leuprorelin, Buserelin, Nafarelin, and Goserelin. Examples of polysaccharides include a glucosaminogly-cane, a hyaluronic acid, a heparin, a low molecular weight heparin or an ultra-low molecular weight heparin or a derivative thereof, or a sulphated polysaccharide, e.g. a poly-sulphated form of the above-mentioned polysaccha-rides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immu-noglobulin molecule or an antigen-binding portion thereof. Examples of antigen-binding portions of immunoglobulin molecules include F(ab) and F(ab')2 fragments, which retain the ability to bind antigen.

The antibody can be polyclonal, monoclonal, recombi-nant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immuno-globulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Anti-body fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) frag-ments, linear antibodies, monospecific or multispecific anti-body fragments such as bispecific, trispecific, tetraspecific and multispecific antibodies (e.g., diabodies, triabodies, tetrabodies), monovalent or multivalent antibody fragments such as bivalent, trivalent, tetravalent and multivalent anti-bodies, minibodies, chelating recombinant antibodies, tri-bodies or bibodies, intrabodies, small modular immunophar-maceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immu-noglobulin domain. As such, immunoglobulin single vari-able domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302).

For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container. As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

An example of a compound to be administered with the drug delivery device disclosed herein is a compound with the INN tirzepatide, as referenced in claim 1 of U.S. Pat. No. 9,474,780.

An example of a pharmaceutical composition to be administered with the drug delivery device disclosed herein is a pharmaceutical composition as referenced in U.S. Pat. No. 11,357,820.

An example of a pharmaceutical composition to be administered with the drug delivery device disclosed herein includes a 0.5 mL solution of 2.5 mg, 5 mg, 7.5 mg, 10 mg, 12.5 mg, or 15 mg of tirzepatide and the following excipients sodium chloride (4.1 mg), sodium phosphate dibasic heptahydrate (0.7 mg), and water for injection. Hydrochloric acid solution and/or sodium hydroxide solution may be added to adjust the pH.

An example starting dosage tirzepatide may be 2.5 mg injected subcutaneously once weekly. After four weeks, the tirzepatide dosage may be increased to 5 mg injected subcutaneously once weekly. The dosage may be further increased in 2.5 mg increments after at least four weeks on the current dose. In an example, the maximum dosage of tirzepatide may be 15 mg injected subcutaneously once weekly. If a dose is missed, patients may be instructed to administer tirzepatide as soon as possible within four days (96 hours) after the missed dose. If more than four days have passed, patients may skip the missed dose and administer the next dose on the regularly scheduled day. In each case, patients may then resume their regular once weekly dosing schedule. The day of weekly administration may be changed, if necessary. The time between two doses may be at least three days (72 hours).

Tirzepatide dosages may include 2.5 mg/0.5 mL, 5 mg/0.5 mL, 7.5 mg/0.5 mL, 10 mg/0.5 mL, 12.5 mg/0.5 mL, and 15 mg/0.5 mL. Tirzepatide may be stored in a refrigerator at 2° C. to 8° C. (36° F. to 46° F.). A single-dose pen or single-dose vial may be stored unrefrigerated at temperatures not to exceed 30° C. (86° F.) for up to 21 days. Tirzepatide may be stored in a carton.

List of Features

10-Device
11-housing
12-cap
13-needle sleeve
17-needle
20-distal region
21-proximal region
22-button
23-piston
200-medicament delivery device
201-body
202-distal end of the body
208-locking member
216-lock ring
217-needle
223-plunger
227-actuation member
228-button
229-dispensing mechanism
232-injection site
240-spring guide
242-protrusions
250-syringe
254-cap
258-stop
260-spring
262-spring
264-clip
265-proximal opening
266-needle shield
267-collar
268-collar
300-medicament delivery device
301-body
302-distal end of body
303-proximal end of body
314-protrusion
316-lock ring
318-portion
319-axially-extending component
320-recess
321-longitudinal axis
326-button
327-actuation member
328-proximal end of the medicament delivery device
330-plunger
332-protrusion
333-recess
334-protrusion
335-recess
250-syringe
354-cap
358-stop
365-proximal opening
400-medicament delivery device
416-lock ring
418-portion 419-axially-extending component
420-protrusion
421-recess
454-cap

The invention claimed is:

1. A medicament delivery device for injecting medicament, wherein the medicament delivery device comprises:
   a body having a proximal end and a distal end defining a longitudinal axis;
   a needle;
   an actuation member movable relative to the body from a first position to a second position for dispensing the medicament via the needle;
   a lock ring rotatable relative to the body from a pre-use position in which movement of the actuation member from the first position to the second position is prevented, to a use position in which a movement of the actuation member from the first position to the second position is permitted;
   an axially-extending component rotationally constrained relative to the lock ring,
   wherein one of the axially-extending component and the lock ring comprises a first protrusion and the other of the axially-extending component and the lock ring comprises a first recess, and wherein the first protrusion is configured to be received in the first recess to constrain rotation of the axially-extending component relative to the lock ring, the axially-extending component being independently rotatable relative to the lock ring prior to engagement of the first protrusion and the first recess; and
   a cap removably attached to the medicament delivery device, wherein the cap comprises a proximally-extending portion configured to engage the axially-extending component to prevent rotation of the lock ring from the pre-use position to the use position when the cap is attached to the medicament delivery device,
   wherein one of the axially-extending component and the proximally-extending portion comprises a second protrusion and the other of the axially-extending component and the proximally-extending portion comprises a second recess, and wherein the second recess is a radially-extending recess extending towards the longitudinal axis and the second protrusion is a radially-extending protrusion extending towards the longitudinal axis and configured to be received in the radially-extending recess to rotationally constrain the proximally-extending portion relative to the axially-extending component when the cap is attached to the medicament delivery device, and wherein the engagement between the second protrusion and the second recess is released upon removal of the cap.

2. The medicament delivery device according to claim 1, wherein the cap is removably attached to the body.

3. The medicament delivery device according to claim 1, wherein the proximally-extending portion of the cap is rotationally constrained relative to the body when the cap is attached to the medicament delivery device.

4. The medicament delivery device according to claim 3, wherein one of the proximally-extending portion of the cap and the body comprises a third protrusion and the other of the proximally-extending portion of the cap and the body comprises a third recess, and
   wherein the cap and the body are configured such that when the cap is attached to the medicament delivery device, the third protrusion is received in the third recess to constrain rotation of the portion of the cap relative to the body.

5. The medicament delivery device according to claim 1, wherein the proximally-extending portion of the cap engages the axially-extending component when the lock ring is in the pre-use position.

6. The medicament delivery device according to claim 1, wherein the axially-extending component and the proximally-extending portion of the cap are located radially inwards from the body.

7. The medicament delivery device according to claim 1, wherein the axially-extending component and the lock ring are separate components.

8. The medicament delivery device according to claim 1, wherein the proximally-extending portion of the cap is configured to prevent rotation of the lock ring relative to the body when the cap is attached to the medicament delivery device.

9. The medicament delivery device according to claim 1, wherein the actuation member is configured to be rotated with the lock ring when the lock ring rotates from the pre-use position to the use position.

10. The medicament delivery device according to claim 1, wherein the actuation member comprises a button configured to be pressed to move the actuation member from the first position to the second position.

11. The medicament delivery device according to claim 1, wherein the medicament delivery device comprises a dispensing mechanism configured to dispense medicament via the needle, and wherein the actuation member is configured to release the dispensing mechanism when the actuation member is in the second position.

12. The medicament delivery device according to claim 1, further comprising a container containing the medicament.

13. The medicament delivery device of claim 1, wherein the axially-extending component is a cylindrical sleeve.

14. A method of preparing a medicament delivery device for use prior to dispensing medicament from the medicament delivery device, the method comprising:

removing a cap from the medicament delivery device, wherein the cap comprises a proximally-extending portion configured to prevent rotation of a lock ring of the medicament delivery device from a pre-use position to a use position; and rotating the lock ring from the pre-use position to the use position, wherein the medicament delivery device comprises:

a body having a proximal end and a distal end defining a longitudinal axis;

a needle;

an actuation member movable relative to the body from a first position to a second position for dispensing the medicament via the needle;

the lock ring rotatable relative to the body from the pre-use position in which movement of the actuation member from the first position to the second position is prevented, to the use position in which a movement of the actuation member from the first position to the second position is permitted;

an axially-extending component rotationally constrained relative to the lock ring, wherein one of the axially-extending component and the lock ring comprises a first protrusion and the other of the axially-extending component and the lock ring comprises a first recess, and wherein the first protrusion is configured to be received in the first recess to constrain rotation of the axially-extending component relative to the lock ring, the axially-extending component being independently rotatable relative to the lock ring prior to engagement of the first protrusion and the first recess; and the cap removably attached to the medicament delivery device, wherein the cap comprises a proximally-extending portion configured to engage the axially-extending component to prevent rotation of the lock ring from the pre-use position to the use position when the cap is attached to the medicament delivery device, wherein one of the axially-extending component and the proximally-extending portion comprises a second protrusion and the other of the axially-extending component and the proximally-extending portion comprises a second recess, and wherein the second recess is a radially-extending recess extending towards the longitudinal axis and the second protrusion is a radially-extending protrusion extending towards the longitudinal axis and configured to be received in the radially-extending recess to rotationally constrain the proximally-extending portion relative to the axially-extending component when the cap is attached to the medicament delivery device, and wherein the engagement between the second protrusion and the second recess is released upon removal of the cap.

15. A method of using a medicament delivery device, the method comprising:

removing a cap from the medicament delivery device, wherein the cap comprises a portion configured to prevent rotation of a lock ring of the medicament delivery device from a pre-use position to a use position;

rotating the lock ring from the pre-use position to the use position; and moving an actuation member from a first position to a second position for dispensing medicament from the medicament delivery device, wherein the medicament delivery device comprises:

a body having a proximal end and a distal end defining a longitudinal axis;

a needle;

an actuation member movable relative to the body from a first position to a second position for dispensing the medicament via the needle;

the lock ring rotatable relative to the body from the pre-use position in which movement of the actuation member from the first position to the second position is prevented, to the use position in which a movement of the actuation member from the first position to the second position is permitted;

an axially-extending component rotationally constrained relative to the lock ring, wherein one of the axially-extending component and the lock ring comprises a first protrusion and the other of the axially-extending component and the lock ring comprises a first recess, and wherein the first protrusion is configured to be received in the first recess to constrain rotation of the axially-extending component relative to the lock ring, the axially-extending component being independently rotatable relative to the lock ring prior to engagement of the first protrusion and the first recess; and the cap removably attached to the medicament delivery device, wherein the cap comprises a proximally-extending portion configured to engage the axially-extending component to prevent rotation of the lock ring from the pre-use position to the use position when the cap is attached to the medicament delivery device, wherein one of the axially-extending component and the proximally-extending portion comprises a second protrusion and the other of the axially-extending component and the proximally-extending portion comprises a second recess, and wherein the second recess is a radially-extending recess extending towards the longitudinal axis and the second protrusion is a radially-extending protrusion extending towards the longitudinal axis and configured to be received in the radially-extending recess to rotationally constrain the proximally-extending portion relative to the axially-extending component when the cap is attached to the medicament delivery device, and wherein the engagement between the second protrusion and the second recess is released upon removal of the cap.

* * * * *